United States Patent [19]

Leibowitz et al.

[11] Patent Number: 4,892,743
[45] Date of Patent: Jan. 9, 1990

[54] NOVEL HYBRID INTERFERON SPECIES

[75] Inventors: Paul J. Leibowitz, Hackensack; Michael J. Ryan, Milford, both of N.J.

[73] Assignee: Schering Corporation, Kenilworth, N.J.

[21] Appl. No.: 564,066

[22] Filed: Dec. 21, 1983

[51] Int. Cl.[4] ............ A61K 45/02; C07K 13/00; C07K 15/26; C12P 21/00
[52] U.S. Cl. .................. 424/85.7; 530/351; 435/69.51
[58] Field of Search ............ 435/68, 172.3; 424/85, 424/85.7; 260/112.5 R, 112 R

[56] References Cited

U.S. PATENT DOCUMENTS 4,456,748 6/1984 Goeddel .................. 435/68

FOREIGN PATENT DOCUMENTS 0032134 7/1981 European Pat. Off. .
A032134 7/1981 European Pat. Off. .
A051873 5/1982 European Pat. Off. .

OTHER PUBLICATIONS

- American BioNuclear, Price List, Sep., 1983.
Goeddel et al., (1980), Nucleic Acids Research, vol. 8, No. 18, pp. 4057–4074.
Weissmann, C. (1981) "The Cloning of Interferon and Other Mistakes, in Interferon 1981", vol. 3, p. 101.
Roberts, T. M. and Gail D. Lauer, 1979, "Maximizing Gene Expression on a Plasmid Using Recombination in Vitro", Methods in Enzymology, 68: pp. 473–482.
Rehberg et al., "Specific Molecular Activities of Recombinant and Hybrid Leukocyte Interferons," J. Biol. Chem., vol. 257 (19), pp. 11497–11502 (1982).
Weber and Weismann, "Formation of Genes Coding for Hybrid Proteins by Recombination Between Related, Cloned Agents in E. Coli," Nucleic Acids Research, vol. 11 (16), pp. 5661–5669 (1983).
Pestka, "The Human Interferons–From Protein Purification and Sequences to Cloning and Expression in Bacteria: Before, Between and Beyond," Archives of Biochem. and Biophys., vol. 221(1), pp. 1–37 (1983).
Pestka, "The Purification and Manufacture of Human Interferons," Scientific American, vol. 249 (2), pp. 29–35 (1983).
Franke et al., "Carboxyterminal Region of Hybrid of Leukocyte Interferons Affects Anti-Viral Specificity," DNA, vol. 1 (3), pp. 223–230 (1982); see C.A. 97: 176172z.
P. K. Weck et al., Antiviral Activities of Hybrids of Two Major Human Leukocyte Interferons, Nucleic Acids Research, vol. 9, No. 22 (1981), pp. 6153–6166.

Primary Examiner—Blondel Hazel
Attorney, Agent, or Firm—Joseph T. Majka; Henry P. Nowak; Gerald S. Rosen

[57] ABSTRACT

The invention features a novel hybrid interferon species that comprises a chain of 161 and/or 162 amino acids. The hybrid is novel not only for its new structure, but also because the hybrid comprises a shortened or truncated segment of alpha interferon, and hence, an entirely new interferon species which is not occurring in nature.

9 Claims, 1 Drawing Sheet (MET) GLN THR HIS SER LEU GLY SER ARG ARG THR LEU MET LEU LEU ALA GLN MET ARG
ARG ILE SER LEU PHE SER CYS LEU LYS ASP ARG HIS ASP PHE GLY PHE PRO GLN GLU
GLU PHE GLY ASN GLN PHE GLN LYS ALA GLU THR ILE PRO VAL LEU HIS GLU MET ILE
GLN GLN ILE PHE ASN LEU PHE THR THR LYS ASP SER SER ALA ALA TRP ASP GLU ASP
LEU LEU ASP LYS PHE CYS THR GLU LEU TYR GLN GLN LEU ASN ASP LEU GLU ALA CYS
VAL MET GLN GLU GLU ARG VAL GLY GLU THR PRO LEU MET ASN ALA ASP SER ILE LEU
ALA VAL LYS LYS TYR PHE ARG ARG ILE THR LEU TYR LEU THR GLU LYS LYS TYR SER
PRO CYS ALA TRP GLU VAL VAL ARG ALA GLO ILE MET ARG SER LEU SER LEU SER THR
ASN LEU GLN GLU ARG LEU ARG ARG LYS GLU

F I G. I

NOVEL HYBRID INTERFERON SPECIES

This application is a continuation-in-part of U.S. application Ser. No. 562,639, filed Dec. 19, 1983 now abandoned.

FIELD OF THE INVENTION

This invention relates to a novel alpha interferon-type protein having interesting antiviral and anti-tumor activities. It contains 161 amino acids, as in a second embodiment 162 amino acids with the addition of methionine arranged in the sequence shown in FIG. 1. The protein can be produced by culturing an organism containing expressable recombinant DNA that codes for the novel alpha interferon-type protein.

BACKGROUND OF THE INVENTION

The antiviral and anti-tumor activity of various interferons is currently being explored. Recently, it has been contemplated to generate hybrid interferons that are not naturally occurring in nature. Such a procedure is shown in U.S. Pat. No. 4,414,150, issued: Nov. 8, 1983.

This invention has advanced the current techniques into further unchartered areas. Rather than dealing with known "whole" segments of interferon, this invention has hybridized, abbreviated, or shortened segments or "sub-segments."

We have found that when the hybrid is formed specifically corresponding to a truncated alpha-2 segment and an alpha-1 segment, the resultant species has a very desirable biological profile.

As is well recognized in the art, the initiation codon ATG has a second meaning corresponding to the presence of the amino acid methionine at the first amino acid in a chain of amino acids comprising a protein. Sometimes the host will cleave this amino terminal methionine off the protein and sometimes not. Our invention contemplates both species. In the former case it will have 161 amino acids and start with glutamine (at the amino terminus) and when the methionine is not cleaved, the resultant protein will have 162 amino acids and the first residue will be methionine.

The new abbreviated interferon species engineered by this invention features a "sub-segment" defined as a delta-4 alpha-2 (Bgl II-1) derived from an alpha-2 sequence, that is joined to a segment defined as (Bgl II) alpha-1 derived from an alpha-1 sequence.

To our pleasant surprise, the above protein features selectively heightened antiviral and anti-tumor activity.

The present invention is characterized as having an antiviral activity of at least $1 \times 10^7$ units/mg as determined by the cytopathic effect-inhibition assay employing EMC virus and human foreskin cells (FS-71) performed essentially as described in a publication by Familletti, et. al. (Reference 1), using as a standard the NIH/WHO uncloned leukocyte interferon standard 69/19.

BRIEF DESCRIPTION OF THE DRAWING

FIG. 1 is an illustration of the amino acid chain of the protein of this invention, which is defined as a delta-4 alpha-2 (Bgl II-1) sub-segment obtained from an alpha-2 interferon sequence followed by an (Bgl II) alpha-1 segment obtained from an alpha-1 interferon sequence. The invention is shown with the presence of an optional amino terminal methionine residue (shown in parenthesis).

SUMMARY OF THE INVENTION

For the purposes of clarification and definition, the gene coding for the novel alpha interferon-type protein(s) is composed of a portion of the amino terminal nucleotide coding sequence from the mature human alpha-2 interferon gene up to the first Bgl II site (hence the phraseology "Bgl II-1") joined to the only Bgl II site found within the coding sequence for the mature human alpha-1 interferon gene. The portion of the human alpha-2 interferon gene used to construct the gene that codes for the invention is missing the first 12 nucleotides that are normally found in the sequence that codes for the mature human alpha-2 interferon and, hence, does not contain genetic information that would code for these first four amino terminal amino acids (CYS-ASP-LEU-PRO); hence, we use the phraseology "delta-4" to reflect this aspect of the sub-segment.

The portion of the human alpha-1 interferon gene used to construct the gene that codes for the invention is comprised of all nucleotides found downstream from the only Bgl II site found in the mature human alpha-1 interferon coding sequence (hence, the phraseology "[Bgl II] alpha-1").

Therefore, we use the phraseology "delta-4 alpha-2 (Bgl II-1)" to describe the nucleotide coding sequence obtained from the mature human alpha-2 interferon gene that was used to construct the gene that codes for the invention, and we use the phraseology "(Bgl II) alpha-1" to describe the nucleotide coding sequence obtained from the mature human alpha-1 interferon gene that was used to construct the gene that codes for the invention. Furthermore, we also define the protein sub-segment and protein segment with this phraseology as well.

For the purposes of definition, mature human alpha-1 interferon is defined as having the amino acid sequence shown below:

---

CYS ASP LEU PRO GLU THR HIS SER LEU ASP ASN ARG ARG THR LEU MET LEU
LEU ALA GLN MET SER ARG ILE SER PRO SER SER CYS LEU MET ASP ARG HIS
ASP PHE GLY PHE PRO GLN GLU GLU PHE ASP GLY ASN GLN PHE GLN LYS ALA
PRO ALA ILE SER VAL LEU HIS GLU LEU ILE GLN GLN ILE PHE ASN LEU PHE
THR THR LYS ASP SER SER ALA ALA TRP ASP GLU ASP LEU LEU ASP LYS PHE
CYS THR GLU LEU TYR GLN GLN LEU ASN ASP LEU GLU ALA CYS VAL MET GLN
GLU GLU ARG VAL GLY GLU THR PRO LEU MET ASN ALA ASP SER ILE LEU ALA
VAL LYS LYS TYR PHE ARG ARG ILE THR LEU TYR LEU THR GLU LYS LYS TYR
SER PRO CYS ALA TRP GLU VAL VAL ARG ALA GLU ILE MET ARG SER LEU SER
LEU SER THR ASN LEU GLN GLU ARG LEU ARG ARG LYS GLU

---

The mature human alpha-2 interferon is defined as having the amino acid sequence shown below:

---

CYS ASP LEU PRO GLN THR HIS SER LEU GLY SER ARG ARG THR LEU MET LEU

-continued

LEU ALA GLN MET ARG ARG ILE SER LEU PHE SER CYS LEU LYS ASP ARG HIS
ASP PHE GLY PHE PRO GLN GLU GLU PHE GLY ASN GLN PHE GLN LYS ALA GLU
THR ILE PRO VAL LEU HIS GLU MET ILE GLN GLN ILE PHE ASN LEU PHE SER
THR LYS ASP SER SER ALA ALA TRP ASP GLU THR LEU LEU ASP LYS PHE TYR
THR GLU LEU TYR GLN GLN LEU ASN ASP LEU GLU ALA CYS VAL ILE GLN GLY
VAL GLY VAL THR GLU THR PRO LEU MET LYS GLU ASP SER ILE LEU ALA VAL
ARG LYS TYR PHE GLN ARG ILE THR LEU TYR LEU LYS GLU LYS LYS TYR SER
PRO CYS ALA TRP GLU VAL VAL ARG ALA GLU ILE MET ARG SER PHE SER LEU
SER THR ASN LEU GLN GLU SER LEU ARG SER LYS GLU

The invention relates to a new species of interferon or protein employing an abbreviated segment or "sub-segment" known as delta-4 alpha-2 (Bgl II-1) derived from an alpha-2 sequence, that is joined to a segment designated as (Bgl II) alpha-1 derived from an alpha-1 sequence.

For the further purpose of definition, the term "segment" shall be defined as a portion of an interferon chain of amino acids that is bounded at one end by a naturally occurring sequence found at one end of the mature molecule.

For the further purpose of definition, the terms "abbreviated segment" or "sub-segment" shall be defined as a portion of an interferon chain of amino acids that is not bounded at either end by either of the naturally occurring sequences found at the ends of the mature molecule and, therefore, is a shortened portion of an interferon amino acid chain that does not comprise the full complement of amino acids that would normally be found at one end in a "segment" of interferon as defined above.

The invention can be further described as a protein having a sequence of 161 or 162 amino acids as defined below:

(MET)$_X$ GLN THR HIS SER LEU GLY SER ARG ARG THR LEU MET LEU LEU ALA
GLN MET ARG ARG ILE SER LEU PHE SER CYS LEU LYS ASP ARG HIS ASP PHE
GLY PHE PRO GLN GLU GLU PHE GLY ASN GLN PHE GLN LYS ALA GLU THR ILE
PRO VAL LEU HIS GLU MET ILE GLN GLN ILE PHE ASN LEU PHE THR THR LYS
ASP SER SER ALA ALA TRP ASP GLU ASP LEU LEU ASP LYS PHE CYS THR GLU
LEU TYR GLN GLN LEU ASN ASP LEU GLU ALA CYS VAL MET GLN GLU GLU ARG
VAL GLY GLU THR PRO LEU MET ASN ALA ASP SER ILE LEU ALA VAL LYS LYS
TYR PHE ARG ARG ILE THR LEU TYR LEU THR GLU LYS LYS TYR SER PRO CYS
ALA TRP GLU VAL VAL ARG ALA GLU ILE MET ARG SER LEU SER LEU SER THR
ASN LEU GLN GLU ARG LEU ARG ARG LYS GLU

Wherein X can be either 0 or 1.

The invention can also be defined as a mixture of first and second proteins having 161 and 162 amino acids, respectively, the second protein differing from the first protein in the addition of methionine to the first amino acid in the above-identified sequence.

The protein or protein mixture is characterized as having at least an antiviral activity of at least $1 \times 10^7$ units/mg as determined by the cytopathic effect-inhibition assay employing EMC virus and human foreskin cells (FS-71) performed essentially as described in a publication by Familletti, et. al (Reference 1), using as a standard the NIH/WHO uncloned leukocyte interferon standard 69/19.

The resulting protein or protein mixture comprises a new interferon species that is not a naturally occurring alpha interferon.

DETAILED DESCRIPTION OF THE INVENTION

Generally speaking, the invention pertains to a protein having a chain or sequence of 161 or 162 amino acids depending on the optional addition of a methionine residue attached to the first amino acid in the sequence. The sequence includes two different portions of naturally occurring alpha interferon as discrete subsequences thereof defined as a sub-segment and segment. The resulting protein is not naturally occuring as an alpha interferon protein.

Referring to FIG. 1, the protein of this invention is illustrated. The protein is shown as a chain of 161 amino acids with the optional addition of methionine attached to the first amino acid of the chain, as depicted in parenthesis in the figure. The invention also contemplates the mixture of these two proteins.

Tests for the above protein or proteins have shown a high activity against viruses and tumors, as compared to the alpha-2 interferon standard currently being commercialized by the present assignee. Of particular interest, the above protein or proteins have demonstrated favorable activity against adenovirus, such as adenovirus-1, and ovarian and cervical carcinomas.

The protein or proteins of the invention have been genetically engineered from two different interferon coding sequences by joining a coding sequence for a sub-segment of mature alpha-2 interferon with a coding sequence for a segment of mature alpha-1 interferon.

The 161 (or 162) amino acid chain of these proteins is theoretically believed to have sulphur-sulphur bonding between the cysteine residue at position twenty-five (or twenty-six) and the cysteine residue at position one hundred and thirty-four (or one hundred and thirty-five), depending upon the optional addition of a methionine residue attached to the first amino acid in the sequence. It is also believed that the biological activity of the inventive protein is related to this disulfide bond, and may also result from the character of the uniquely combined sequence provided for by the segment and sub-segment derived from the alpha-1 and alpha-2 mature coding sequence, respectively.

Introduction and General Plan

The general method for making this novel alpha interferon-type protein was to prepare a hybrid interferon gene that codes for the novel alpha interferon-type protein. This first entailed the joining of a group of promoters with translation initiation signals to the start of the mature alpha-2 interferon coding sequence. Subsequently, DNA fragments in which the promoters had been joined to the alpha-2 amino terminal coding sequences (up to the first Bgl II restriction site) were identified, isolated, and ligated to the carboxy terminal coding sequences of the alpha-1 interferon gene that immediately following the Bgl II site found in the mature alpha-1 coding sequences.

The actual experiments performed can be grouped into six broad activity areas: (1) construction of a derivative of the alpha-1 interferon plasmid Hif-2h (Reference 2) that has only one Eco RI site, rather than two; (2) the assembly of a group of promoters that end in an ATG translation initiation codon and differ in the number of nucleotides between the "Shine-Dalgarno" sequence and this initiation codon; (3) the joining of this group of promoters to the amino-terminal coding sequences of the alpha-2 interferon gene; (4) the isolation of DNA fragments which included the promoter regions ligated to the amino-terminal coding sequences of the alpha-2 interferon gene; (5) the joining of these promoter-containing fragments to the carboxy-terminal alpha-1 interferon coding sequences; and (6) the screening of bacterial clones for the production of active hybrid interferon.

The method use for transforming E. coli was essentially as described (Reference 13). Restriction enzymes, T4 DNA ligase, and any other DNA modifying enzymes obtained from New England Biolabs and Bethesda Research Laboratories were used generally according to the manufacture's recommendations. Methods for recovering DNA from gels were generally according to those reviewed by H. O. Smith: Smith, H. O. (1980) "Recovery of DNA from gels," Methods in Enzymology, Vol. 65, Part I, edited by Grossman, L. and K. Moldave. Academic Press, N. Y. 371–380. Protocols for methods and procedures not specifically described below (or essentially equivalent substitutes) can be found in a number of available "recipe books." For example: Maniatis, T., E. F. Fritsch, and J. Sambrook. "Molecular Cloning—A Laboratory Manual" (1982), published by the Cold Spring Harbor Laboratory, Cold Spring Harbor, N.Y. Each of these above "steps" is described in more detail below.

1. Deletion of a non-coding region (including an Eco RI site) beyond the end of the alpha-1 IF gene. The alpha-1 interferon coding sequence is contained in the plasmid designated Hif-2h (Reference 2) which has two Eco RI sites. An aliquot of this plasmid DNA was subjected to digestion with restriction endonuclease Eco RI under conditions that would be expected to produce some partial digestion products. The exposed ends were trimmed with nuclease SI followed by a total digestion with Bam HI. The desired DNA fragment, which carried the alpha-1 interferon gene up to the former Eco RI site in the non-coding region as well as the amino-terminal coding end of the tetracycline resistance gene, was identified by its mobility on an agarose gel relative to markers of known size and isolated. In parallel, pBR322 (Reference 3) DNA was digested with Pst I followed by treatment with nuclease SI and finally Bam HI digestion. In this case, the fragment that was isolated carried the origin of replication for pBR322 as well as the carboxy terminal coding sequences for the tetracycline resistance gene. The above two fragments were enzymatically joined with T4 DNA ligase, and the recombinant DNA was used to transform the E. coli strain 294 (Reference 4). Plasmid DNA from tetracycline-resistant transformants was subjected to restriction enzyme analysis to verify the structure, in which there is only one Eco RI site that is upstream of the alpha-1 interferon coding sequence.

2. Construction of a family of promoters carrying both a "Shine-Dalgarno" sequence and an ATG translation initiation codon. A plasmid was constructed in which there was a unique Eco RI restriction site approximately 30 base pairs upstream from the sequence . . . CCTCGCCCTTTGCTTTACTGATGGTCC . . . (obtained from the "leader" coding sequence of the alpha-1 interferon gene in the plasmid Hif-2h). This plasmid was constructed by cloning a forty base-pair fragment of DNA (i.e., the Hae III/Pvu II restriction fragment found within the coding region for the leader sequence for the human alpha-1 interferon gene of Hif-2h) between the Hind III and Pvu II sites of pBR322 in the orientation that regenerated the Pvu II site.

Aliquots of this plasmid DNA were first linearized by enzymatic digestion at the unique Eco RI restriction site. Then, varying numbers of nucleotides between this point and the above (underlined) ATG codon were removed by different extents of nuclease digestion using Exonuclease III followed by nuclease SI or, in another experiment, with nuclease Bal 31 generally following published procedures (such as, for example, Reference 6 and also Maniatis, T., E. F. Fritsch, and J. sambrook. "Molecular Cloning—A Laboratory Manual" [1982], published by the Cold Spring Harbor Laboratory, Cold Spring Harbor, N.Y.) and/or the manufacturer's recommendations. These trimmed DNA molecules were ligated to a nominally 125 base pair lac UV5 promoter (derived from pKB252 [Reference 5]) fragment that carries the "Shine-Dalgarno" sequence for translation initiation. The sequence of this promoter fragment is as follows:

5'-GAATTCCAGTGAATCCGTAATCATGGT-
CATAGCTCACTCATTAGGCACC-
CCAGGCTTTACACTTT
ATGCTTCCGGCTCGTATAATGTGT-
GGAATTGTGAGCGGATAACAATTT-
CACACAGGAAACAG-3'

The resulting population of recombinant DNA molecules was used to transform the E. coli strain 294 to ampicillin-resistance. Plasmid DNA was isolated from a population of these ampicillin-resistant bacteria and used for the isolation of a family of lac promoters that should carry a promoter, operator, Shine-Dalgarno sequence, and end with the translation initiation codon, ATG. The members of this family differ from one another in the number of nucleotides between the Shine-Dalgarno sequence and the ATG codon and, therefore, are expected to have different efficiencies of translation initiation (References 4, 6, and 7).

An aliquot (58 ug) of this DNA (containing the family of lac promoters) isolated from a non-methylating E. coli strain was digested with the restriction endonuclease Ava II (which recognizes the nucleotide sequence GG(A/T)CC and cleaves each strand of the DNA between the G residues) in a reaction volume of 250 ul. After this digestion, the sample was placed on ice and 30 ul of 10X S1 salts (1.5M NaCl, 0.5M sodium acetate pH 4.0, 0.06M ZnSO4), 20 ul 5M NCl, and 2 ul (200 units) of nuclease S1 (Sigma catalog #N-5255) were added and incubated at 11° C. for ten minutes. To this reaction 0.5 ml of (0.3M sodium acetate, 0.01M EDTA, 0.2M tris HCl pH 9.5) was added, and the DNA precipitated by addition of 2.5 volumes of ethanol. The pelleted DNA was resuspended in an appropriate buffer and digested with Eco RI. The products of this reaction were analyzed on an acrylamide gel, and the population of DNA fragments that carried the promoter and translation initiation sequences was observed as a broad DNA band of (approximately) ≧125 base pairs in length. Within this group was a collection of fragments that have a cleaved Eco RI site at one end and an ATG codon at the other, flush, end that serves as a translation initiation signal. This entire collection of DNA fragments was isolated from the acrylamide gel to be joined to the amino terminal coding end of the alpha-2 interferon gene in the next steps, described below.

3. Joining of the promoter fragments to the amino-terminal coding region for the alpha-2 interferon gene. The starting material for this step included an alpha-2 IF gene in which a Hind III restriction site had been placed at the start of the mature alpha-2 coding sequence creating the nucleotide sequence AAGCTTGT . . . The underlined codon (TGT) codes for cysteine which is the first amino acid of the mature alpha-2 interferon species. A description of this type of construction is presented in Reference 8 (FIG. 9, Structures 1-3). This alpha-2 interferon gene-containing plasmid also had a unique Eco RI site upstream of this unique Hind III site.

Therefore, sequential digestions of this DNA with Hind III, nuclease S1, and RI would yield a vector into which the lac promoters (prepared in step #2, above) could be joined in a predetermined orientation. Specifically, fifty micrograms of this alpha-2 interferon gene-containing plasmid were digested to completion with Hind III in a 350 ul reaction. The sample was transferred to ice and 50 ul of 10X S1 salts, 35 ul of 5M NaCl, and 2 ul (200 units) of nuclease S1 were added. This mixture was incubated at 11° C. for 10 minutes after which 0.4 ml of (0.3M sodium acetate, 0.01M EDTA, 0.2M tris HCl pH 9.5) was added and the DNA precipitated by the addition of 2.5 volumes of ethanol. After this DNA was resuspended, it was digested with Eco RI after which the enzyme was inactivated by heating at 65° C. The DNA was again precipitated with ethanol and finally resuspended and enzymatically joined by T4 DNA ligase to the collection of promoters isolated above. The recombinant DNA molecules were then used to transform E. coli strain D1210 (References 9 and 13) to ampicillin resistance.

4. Isolation of DNA fragments containing the lac promoter joined to the amino-terminal coding region of the mature alpha-2 interferon gene. Plasmid DNA was isolated from an entire population of ampicillin-resistant transformants of D1210 obtained in step 3 and a 60 microgram aliquot was subjected to digestion with the restriction endonucleases Eco RI and Bgl II. The products of this reaction were electrophoresed on an 8% polyacrylamide gel. As expected, there was a broad, fuzzy, band of fragments approximately 330±20 base pairs in length. These fragments, therefore, were expected to contain lac transcription and translation initiation signals fused to the amino terminal coding region (as far as the first Bgl II site) of the alpha-2 interferon gene. The broad band encompassing this group of fragments was isolated from the gel.

5. Formation of the alpha-2/alpha-1 hybrid interferon gene. An aliquot of the alpha-1 IF gene containing plasmid DNA constructed in step 1 was digested with the restriction endonucleases Eco RI and Bgl II, and the larger of the two fragments (which carries the carboxy terminal coding region for the alpha-1 interferon as well as the gene for the tetracycline resistance) was isolated after agarose gel electrophoresis. This larger DNA fragment was then ligated to the population of lac promoter fragments isolated in step #4.

6. Isolation and characterization of a clone expressing a hybrid interferon with antiviral activity. The ligated DNA molecules found in the previous step (which should have the lac regulatory elements fused to an alpha-2/alpha-1 hybrid interferon gene) were used to transform the E. coli strain 294 to tetracycline resistance. Individual colonies were picked, grown, and extracts prepared. These extracts were assayed for the presence of interferon activity using procedures essentially as described in the literature (References 1 and 10).

Plasmid DNA was isolated from the clone producing the highest level antiviral activity. The junction between the lac promoter and the amino terminal coding end of this hybrid interferon coding sequence was then subjected to DNA sequence analysis. This revealed, unexpectedly, that the coding sequence for the first four amino acids had been removed during the constructions described above, presumably due to the "fraying" activity known to be associated occasionally with the single strand nuclease S1 on the ends of linear duplex DNA molecules (Reference 6). A partial nucleotide sequence from this region is presented below:

```
                  (fmet) Gln  Thr  His  Ser  Leu
. . . AGGAAACAGACTG ATA  CAA  ACC  CAC  AGC  CTG . . .
```

A Preferred Method for the Construction and Expression of a Delta-4 Alpha-2 (Bgl II-1)/(Bgl II) Alpha-1 Hybrid Interferon Gene A preferred method embodiment for the construction of this interferon gene is hereinafter described. This method is also more flexible, since it will allow the incorporation of different genetic regulatory sequences.

The starting materials for this construction would include a derivative of the alpha-2 interferon gene with a Hind III restriction endonuclease site at the start of the mature coding sequence as mentioned above and described in the literature (Reference 8) and the aforementioned (Bgl II) alpha-1 fragment. The procedure would involve the isolation of a (nominally) 276 base pair Hind III/Pvu II fragment from this alpha-2 interferon gene-containing plasmid which would span the region of interest. This fragment would then be annealed with a synthetic oligonucleotide (which can be custom synthesized commercially), for example, fifteen nucleotides long having the following sequence:

5'-CAAACCCACAGCCTG-3'

The kinased oligonucleotide should be annealed to a template (which should be a heat denatured Hind III/Pvu II DNA fragment described above which includes a portion of the nucleotide coding sequence for the mature human alpha-2 interferon gene). The synthetic oligonucleotide will form a duplex DNA structure starting with the first nucleotide of the codon for the fifth amino acid of the mature alpha-2 interferon. The concerted action of the polymerase and 3'-5' exonuclease activities of the Klenow fragment of the E. coli DNA polymerase I, in the presence of the four deoxynucleoside triphosphates, followed by digestion with Bgl II will release the amino terminal end (up to the first Bgl II site) of alpha-2 interferon, but lacking the first four amino acids. The desired fragment can be readily visualized by autoradiography if, for example, the oligonucleotide had been kinased with gamma-$^{32}$P-ATP. Protocols for each of these steps can be found in the literature (Reference 11).

The alpha-1 fragment recipient plasmid described above can be digested with Eco RI and then "filled in" with, for example, the Klenow fragment of DNA polymerase in the presence of the four dNTP's and then digested with Bgl II. Removal of the 5'-terminal phosphates at this point is recommended to decrease the background in the following steps. The larger fragment produced by these manipulations would then be ligated to the amino terminal coding region of alpha-2 isolated in the step above. The recombinant DNA formed and isolated after transformation of a suitable E. coli host and selection of tet®) clones) will, therefore, have an Eco RI site immediately before the start of the delta-4 alpha-2 (Bgl II-1/Bgl II) alpha-1 interferon structural gene. This gene can be expressed in a number of ways: for example, the molecule could be digested by Eco RI followed by any one of a number of single strand specific nucleases (Reference 12) to generate a flush end against which one could ligate a flush-ended fragment containing a promoter, ribosome binding site, and ending with a translation initiation codon. Producing clones will be those in which the regulatory elements are in the correct orientation relative to the coding sequence for the subject species.

The subject species is preferably administered parenterally (e.g., intravenously, subcutaneously, intramuscularly) to patients using methods and dosages similar to those used for human alpha-2 interferon. We also contemplate that the subject species will be useful when applied topically (e.g., corneal applications to treat susceptible viral eye infections).

It is contemplated that dosages from $10^5$-$10^8$ U/M$^2$ body surface area/day will be appropriate but that the attending physician will determine the correct dose dependent upon the particular patient and the precise condition under treatment. A suitable formulation is described in European Patent Application No. 82481, published June 29, 1983.

APPENDIUM OF REFERENCES

1. Familletti, Philip C., Sara Rubenstein, and Sidney Pestka. 1981. Methods in Enzymology, 78:387–394, Academic Press Inc.
2. Mantei, N., M. Schwarzstein, M. Streuli, S. Panem, S. Nagata, and C. Weissmann. 1980. The nucleotide sequence of a cloned human leukocyte interferon cDNA. Gene 10:1-10.
3. Bolivar, F., R. L. Rodriguez, P. J. Green, M. C. Betlach, H. L. Heyneker, H. W. Boyer, J. H. Crosa, and S. Falkow 1977. Construction and characterization of new cloning vehicles. II. A multi-purpose cloning system. Gene 2:95.
4. Backman, K. and M. Ptashne. 1978. Maximizing Gene Expression on a Plasmid Using Recombination in Vitro. Cell 13:65-71.
5. Backman, K., M. Ptashne, and W. Gilbert. 1976. Construction of plasmids carrying the CI gene of bacteriophage lambda. Proc. Nat. Acad. Sci. 73:4174-4178.
6. Roberts, Thomas M. and Gail D. Lauer. 1979. Maximizing Gene Expression on a Plasmid Using Recombination in Vitro. Methods in Enzymology, 68:473-482, Academic Press Inc.
7. Roberts, Thomas M., Raymond Kacich, and Mark Ptashne. 1979. A general method for maximizing the expression of a cloned gene. Proc. Nat. Acad. Sci., Vol. 76, No. 2, pp. 760–764.
8. Weissmann, C. (1981) The Cloning of Interferon and Other Mistakes, in Interferon 1981, Volume 3, p. 101, edited by Ion Gresser, Academic Press, N.Y.
9. Sadler, J. R., M. Tecklenburg, and J. L. Betz. 1980. Plasmids Containing Many Tandem Copies of a Synthetic Lactose Operator. Gene 8:279-300.
10. Nagata, S., H. Taira, A. Hall, L. Johnsrud, M. Streuli, J. Ecsodi, W. Boll, K. Cantell, and C. Weissmann. 1980. Synthesis in E. coli of a polypeptide with human leukocyte interferon activity. Nature 284:316-320.
11. Goeddel, David V., H. Michael Shepard, Elizabeth Yelverton, David Leung, and Roberto Crea. 1980. Synthesis of human fibroblast interferon by E. coli. Nucleic Acids Res., Vol. 8, No. 18, pp. 4057–4074.
12. Protocols for methods and procedures not specifically described above or essentially equivalent substitutes can be found in a number of available "recipe books." For example: Maniatis, T., E. F. Fritsch, and J. Sambrook. "Molecular Cloning—A Laboratory Manual" (1982), published by the Cold Spring Harbor Laboratory, Cold Spring Harbor, N.Y.
13. Dagert, M. and S. D. Ehrlich. 1979. Prolonged Incubation in Calcium Chloride Improves the Competence of Escherichia coli Cells. Gene 6:23-28.

Having thus described the invention, what is desired to be protected by Letters Patent is presented by the following appended claims.

What is claimed is:

1. A protein having an amino acid sequence of 161 or 162 amino acids depending on the optional addition of methionine attached to a first amino acid in said sequence, said sequence including different portions of two different naturally occurring alpha interferons as joined discrete sub-sequences thereof defined as a delta-4 alpha-2 (Bgl II-1) sub-segment and an (Bgl II) alpha-1 segment, wherein said protein is a chain of amino acids that is not naturally occurring as an alpha interferon.

2. The protein of claim 1, wherein said delta-4 alpha-2 (Bgl II-1) sub-segment precedes said (Bgl II) alpha-1 segment in said chain.

3. A mixture of first and second proteins, said first protein having an amino acid sequence of 161 amino acids and said second protein having a sequence of 162 amino acids and differing from said first protein by addition of methionine attached to a first amino acid in said sequence, sequences of said first and second proteins including different portions of two different naturally occurring alpha interferons as joined discrete sub-sequences thereof defined as delta-4 alpha-2 (Bgl II-1) sub-segment and an (Bgl II) alpha-1 segment, wherein said proteins are each a chain of amino acids that is not naturally occurring as an alpha interferon.

4. A protein comprising a sequence of 161 or 162 amino acids as defined below:

(MET)$_X$ GLN THR HIS SER LEU GLY SER ARG ARG THR
LEU MET LEU LEU ALA GLN MET ARG ARG ILE SER
LEU PHE SER CYS LEU LYS ASP ARG HIS ASP PHE
GLY PHE PRO GLN GLU GLU PHE GLY ASN GLN PHE
GLN LYS ALA GLU THR ILE PRO VAL LEU HIS GLU
MET ILE GLN GLN ILE PHE ASN LEU PHE THR THR
LYS ASP SER SER ALA ALA TRP ASP GLU ASP LEU
LEU ASP LYS PHE CYS THR GLU LEU TYR GLN GLN

-continued

| |
|---|
| LEU ASN ASP LEU GLU ALA CYS VAL MET GLN GLU |
| GLU ARG VAL GLY GLU THR PRO LEU MET ASN ALA |
| ASP SER ILE LEU ALA VAL LYS LYS TYR PHE ARG |
| ARG ILE THR LEU TYR LEU THR GLU LYS LYS TYR |
| SER PRO CYS ALA TRP GLU VAL VAL ARG ALA GLU |
| ILE MET ARG SER LEU SER LEU SER THR ASN LEU |
| GLN GLU ARG LEU ARG ARG LYS GLU |

Where X can be either 0 or 1, and further wherein said protein has an antiviral activity of at least about $1\times10^7$ units/mg as determined by the cytopathic effect-inhibition assay.

5. A mixture of first and second proteins each comprising a sequence of 161 amino acids as defined below:

| |
|---|
| GLN THR HIS SER LEU GLY SER ARG ARG THR LEU |
| MET LEU LEU ALA GLN MET ARG ARG ILE SER LEU |
| PHE SER CYS LEU LYS ASP ARG HIS ASP PHE GLY |
| PHE PRO GLN GLU GLU PHE GLY ASN GLN PHE GLN |
| LYS ALA GLU THR ILE PRO VAL LEU HIS GLU MET |
| ILE GLN GLN ILE PHE ASN LEU PHE THR THR LYS |
| ASP SER SER ALA ALA TRP ASP GLU ASP LEU LEU |
| ASP LYS PHE CYS THR GLU LEU TYR GLN GLN LEU |
| ASN ASP LEU GLU ALA CYS VAL MET GLN GLU GLU |
| ARG VAL GLY GLU THR PRO LEU MET ASN ALA ASP |
| SER ILE LEU ALA VAL LYS LYS TYR PHE ARG ARG |
| ILE THR LEU TYR LEU THR GLU LYS LYS TYR SER |
| PRO CYS ALA TRP GLU VAL VAL ARG ALA GLU ILE |
| MET ARG SER LEU SER LEU SER THR ASN LEU GLN |
| GLU ARG LEU ARG ARG LYS GLU | said second protein differing from said first protein by a methionine attached to a first amino acid in said above defined sequence, and wherein said mixture has an antiviral activity of at least $1\times10^7$ units/mg as determined by the cytopathic effect-inhibition assay.

6. A protein comprising an amino acid sequence of 161 or 162 amino acids depending on the optional additional of methionine attached to a first amino acid in said sequence, said sequence including different portions of two different naturally occurring alpha interferons as joined discrete sub-sequences thereof, defined as a delta-4 alpha-2 (Bgl II-1) sub-segment and an (Bgl II) alpha-I segment, wherein said protein is a chain of amino acids that is not naturally occurring as an alpha interferon, and characterized as having an antiviral activity of at least $1\times10^7$ units/mg as determined by the cytopathic effect-inhibition assay.

7. The protein of claim 6 wherein said delta-4 alpha-2 (Bgl II-1) sub-sequence precedes said (Bgl II) alpha-1 segment in said chain.

8. A protein having an amino acid sequence of 161 or 162 amino acids depending on the optional addition of methionine attached to a first amino acid in said sequence, said sequence including two different portions of naturally occurring alpha interferon as joined discrete sub-sequences thereof defined as a sub-segment and segment, wherein said protein is a chain of amino acids that is not naturally occurring as an alpha interferon and wherein said protein is missing the first four amino terminal amino acids.

9. The protein of claim 8 wherein said protein has an antiviral activity of at least $1\times10^7$ units/mg as determined by the cytopathic effect-inhibition assay.

* * * * *